United States Patent [19]

Samson et al.

[11] Patent Number: 4,573,470

[45] Date of Patent: Mar. 4, 1986

[54] LOW-PROFILE STEERABLE INTRAOPERATIVE BALLOON DILITATION CATHETER

[75] Inventors: Wilfred J. Samson, Saratoga; Jeffrey S. Frisbie, San Jose, both of Calif.

[73] Assignee: Advanced Cardiovascular Systems, Inc., Mountain View, Calif.

[21] Appl. No.: 615,141

[22] Filed: May 30, 1984

[51] Int. Cl.$^4$ .............................................. A61M 29/02
[52] U.S. Cl. .................................... 128/344; 128/657; 128/772; 604/96
[58] Field of Search ............... 128/344, 343, 772, 657; 604/95, 96, 97, 98, 99, 100, 101, 102, 164, 165, 171

[56] References Cited

U.S. PATENT DOCUMENTS

| | | | |
|---|---|---|---|
| 3,503,385 | 3/1970 | Stevens | 128/657 |
| 3,552,384 | 1/1971 | Pierie et al. | 128/657 |
| 4,292,974 | 10/1981 | Fogarty et al. | 604/98 |
| 4,332,254 | 6/1982 | Lundquist | 128/344 |
| 4,338,942 | 7/1982 | Fogarty | 604/99 |
| 4,403,612 | 9/1983 | Fogarty | 128/344 |
| 4,422,447 | 12/1983 | Schiff | 128/344 |

Primary Examiner—Gene Mancene
Assistant Examiner—Cary E. Stone
Attorney, Agent, or Firm—Flehr, Hohbach, Test, Albritton and Herbert

[57] ABSTRACT

Low-profile steerable intraoperative balloon dilatation catheter with a flexible core wire having proximal and distal extremities. A flexible tube extends over the core wire and has proximal and distal extremities with the distal extremity being bonded to the distal extremity of the core wire to form a liquid-tight seal. A balloon is carried by the distal extremity of the flexible tube. The flexible tube provides a lumen extending from its proximal end into the balloon. An adapter is secured to the proximal ends of the core wire and the flexible tube. The adapter has at least first and second arms with the core wire extending through the first arm and the lumen being in communication with the second arm. A rotation limiter is carried by the first arm and is secured to the core wire and permits rotation of the core wire while limiting its movement longitudinally of the axis of the core wire. The catheter has a length so that there is approximately a one-to-one correspondence in rotation of the tip of the core wire with the rotation of the core wire at the proximal extremity.

4 Claims, 3 Drawing Figures

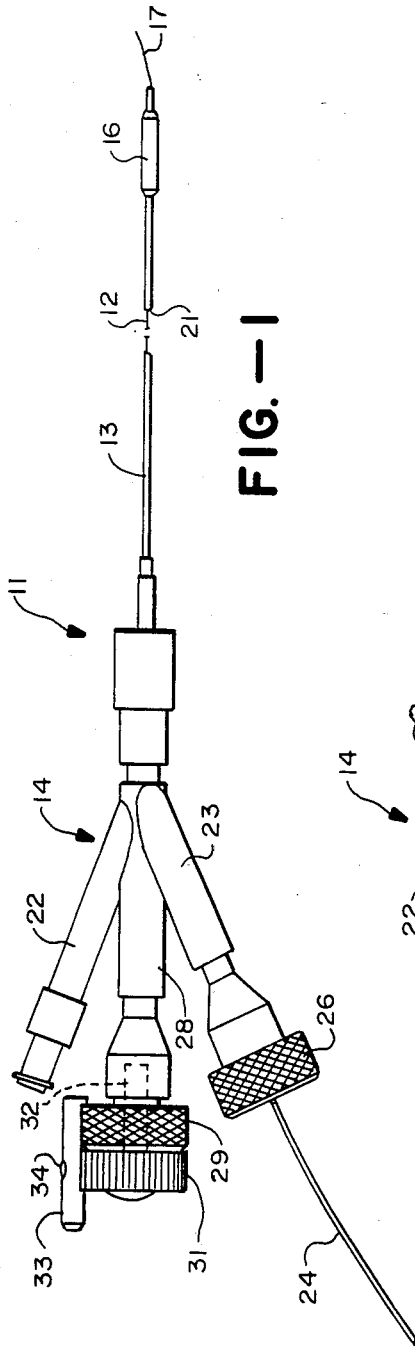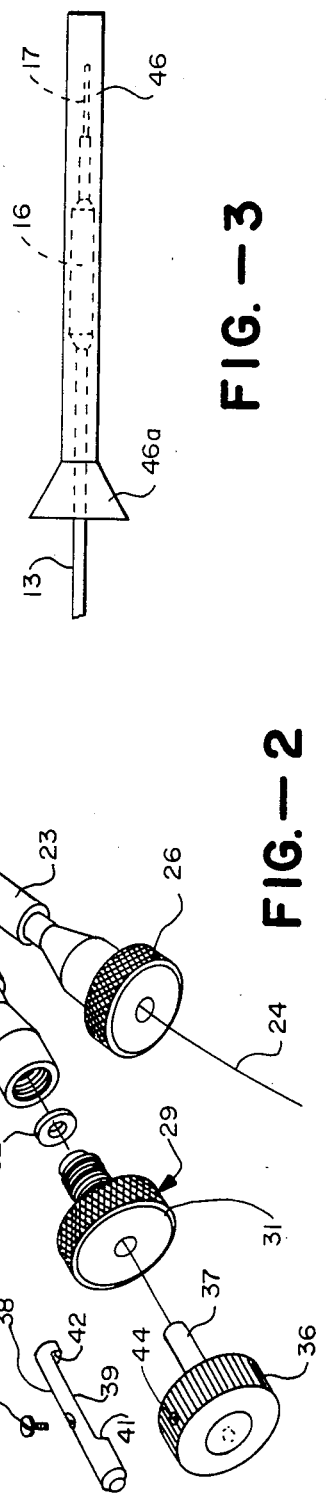

LOW-PROFILE STEERABLE INTRAOPERATIVE BALLOON DILITATION CATHETER

This invention relates to balloon dilatation catheters and more particularly to a low-profile steerable intraoperative balloon dilatation catheter.

During arterial bypass surgery, it has been found that vascular stenosis often may be better treated by utilization of a dilatation catheter rather than by a grafting operation. Although balloon-type dilatation catheters have heretofore been provided, none have been particularly adapted for adjunctive dilatation of small diameter vascular stenosis during arterial bypass surgery. There is therefore a need for a new and improved balloon dilatation catheter which particularly lends itself to surgical cases in which surgical bypass of a vascular stenosis is not possible due to the size and/or location of the lesion.

In general, it is an object of the present invention to provide a low-profile steerable intraoperative balloon dilatation catheter which can be utilized in conjunction with arterial bypass surgery to dilate a vascular stenosis.

Another object of the invention is to provide a catheter of the above character which can be readily used by the surgeon.

Another object of the invention is to provide a catheter of the above character which can be constructed with ease.

Additional objects and features of the invention will appear from the following description in which the preferred embodiment is set forth in detail in conjunction with the accompanying drawing.

FIG. 1 is a side elevational view of a low-profile steerable intraoperative balloon dilatation catheter incorporating the present invention.

FIG. 2 is a partial isometric exploded view of the adapter used on the dilatation catheter shown in FIG. 1.

FIG. 3 is an enlarged side elevational view of the distal extremity of the dilatation catheter shown in FIG. 1 covered with a protective sheath.

The low-profile steerable intraoperative balloon dilatation catheter is comprised of a flexible core wire having proximal and distal extremities. A flexible tubular member extends over the core wire and has proximal and distal extremities with the distal extremity being bonded to the distal extremity of the core wire to form a liquid-tight seal. A balloon is carried by the distal extremity of the flexible tubular member. The flexible tubular member provides an annular passage or lumen extending from its proximal end into the balloon. An adapter is secured to the proximal ends of the flexible core wire and the flexible tubular member. The adapter has a central arm and two side arms. The two side arms are in communication with the lumen extending into the balloon. The core wire extends through the central arm so it can be used to facilitate insertion of the dilatation catheter into a vascular passage.

More, in particular, as shown in the drawing, the low-profile steerable intraoperative balloon dilatation catheter 11 has many characteristics which are similar to the low-profile steerable dilatation catheter disclosed in co-pending application Ser. No. 615,118, filed May 30, 1984. It consists of a core wire 12 formed of a suitable material such as stainless steel. The core wire can be dimensioned in the manner described in co-pending application Ser. No. 615,118 filed May 30, 1984. However, it has a length which is substantially less than the length disclosed in said co-pending application, as for example, 40 centimeters rather than 150 centimeters. In addition, if desired, it can have a lesser cross-sectional area because of the shorter length and the lesser requirement for torsional rigidity.

A flexible tubular member 13 extends over the core wire 12. The proximal extremities of the core wire 12 and the tubular member 13 are coupled to a triple arm adapter 14. The distal extremity of the tubular member 13 carries a balloon 16. If desired, the balloon 16 can be formed integral with the tubular member 13 in a manner well known to those skilled in the art. The extreme distal extremities of the tubular member 13 and the core wire 12 are bonded to each other to form a liquid-tight seal. The balloon and the liquid-tight seal can be formed in a manner described in co-pending application Ser. No. 522,835 filed on Aug. 12, 1983. A flexible tip 17 can be provided on the distal extremity of the core wire 12 also in a manner described in co-pending application Ser. No. 522,835 filed on Aug. 12, 1983.

The tubular member 13 in conjunction with the core wire 12 provides an annular flow passage or lumen 21 which extends from the balloon into the triple arm adapter 14 and is in communication with the two side arms 22 and 23 of the adapter 14. A bleed wire or vent tube 24 extends through the side arm 23 and extends into the distal extremity of the balloon 16 so that when a radio contrast liquid is introduced through the side arm 22, air in the balloon can pass out through the vent tube 24. The side arm 23 is provided with a knurled knob 26 which can be adjusted to open and close an O-ring (not shown) with respect to the vent tube 24 and to form a liquid-tight seal with respect to the vent tube 24.

The core wire 12 extends through the central arm 28 of the triple arm adapter 14. The central arm is provided with a thumb screw 29 having a knurled knob 36. The thumb screw 29 is adapted to engage an O-ring 32 to form a liquid-tight seal with respect to the core wire 12.

Means is provided for imparting rotational movement to the core wire 12 and consists of a knob 31 which has the core wire 12 bonded therein so that as the knob 36 is rotated, the core wire 12 will be rotated. The knob 36 is provided with a smooth-surfaced extension 37 which is rotatably mounted in the thumb screw 29. Pop-out stop and rotation limiting means 33 is provided for limiting movement axially or longitudinally of the axis of the knob 36 while still permitting rotational movement of the knob 36. This means consists of a stop and limiting member 38. The member 38 can be of any desired shape. The member 38 is provided with a cutout 39 to form spaced-apart parallel lips 41 and 42. The member 38 is mounted on one of the knobs 31 and 36 and as shown is mounted on the knob 36 with the cutout 39 facing the knob 36 by a screw 43 threaded into a hole 44 in the knob 36. The lip 41 overlies the knob 36 and the lip 42 underlies the knob 31. The engagement of the member 38 with the knobs 31 and 36 prevents movement of the knob 36 longitudinally of its axis of rotation and away from the knob 31 while permitting rotational movement of the knob 36.

Since the catheter is utilized for intraoperative procedures, the catheter is substantially shorter than dilatation catheters and can have a length of approximately 40 centimeters. The core wire 12 and the tubular member 13 are sized accordingly. The core wire can have a diameter of 0.010 inches.

A protective sheath 46 with a funnel-shaped entrance 46a is provided on the distal extremity of the catheter and is removable. It serves to protect the balloon 16 and the tip 17 prior to use of the catheter. The funnel shaped entrance 46a facilities placement of the sheath 46 on the catheter.

Operation and use of the low-profile steerable intraoperative balloon dilatation catheter may now be briefly described as follows.

Let is be assumed that a bypass operation is being performed and that it is found that a surgical bypass of a vascular stenosis is not possible or desirable due to the size and/or location of the lesion. Prior to the bypass surgery, all equipment to be used in the procedure should be prepared. The balloon 16 of the catheter should be tested to a maximum pressure as, for example, 90 psi prior to commencement of the procedure. Typically the balloon can be inflated with a sterile saline solution. However, if intraoperative X-ray or fluoroscopy is to be utilized, the balloon should be filled utilizing a 60% contrast medium.

The protective sheath 46 is slid off of the balloon 16. A 10 cc syringe can be connected to the balloon inflation arm 22 and the balloon inflated with air. The knurled screw 26 mounted on the side arm 23 is loosened and a vent tube or wire 24 is inserted into the same and carefully advanced into the lumen 21 until it reaches the balloon 16 and is near the distal extremity of the balloon 16. Thereafter the thumb screw 26 is adjusted until the O-ring (not shown) is almost but not quite closed around the vent tube.

A balloon inflating device such as that described in U.S. Pat. No. 4,439,185 and called an Indeflator is filled with approximately 6 to 10 cc of a balloon inflation medium utilizing a conventional contrast medium. Holding the adapter 14 so that the inflation arm 23 is at the bottom, the contrast liquid is introduced into the arm 23 by the Indeflator. The thumb screw 26 is closed to ensure that the inflation medium does not leak around the vent tube 24. Then while keeping the balloon 16 at a level above the adapter, the balloon 16 is slowly filled with the inflation medium by maintaining a constant pressure. As the balloon is filled the air is removed from the balloon by the vent tube 24. After the balloon and the lumen 21 leading to the balloon have been completely filled with the contrast medium, the vent tube 24 can be withdrawn from the balloon. To facilitate this removal, the thumb screw 26 may have to be loosened. Typically the vent tube 24 can be removed and discarded. However, if it is desired to utilize the vent tube as a stiffner for the shaft of the catheter, the vent tube can be withdrawn until its distal extremity is approximately 5 centimeters from the balloon 16. The proximal extremity of the vent tube can then be looped and inserted through the O-ring and closed off by closing the thumb screw 26.

Prior to insertion of the dilatation catheter into and withdrawing it from the artery and the stenosis in the artery, a negative pressure must be maintained on the balloon 16 to keep it totally deflated to its minimum size.

The extent and degree of stenosis to be dilated are shown by the preoperative angiogram. Operative calibration before dilatation, however, will confirm the angiographic finding and will provide an accurate measurement of the distance to the stenosis from the arteriotomy.

To facilitate the correct positioning of the balloon 16 in the stenosis, an adjustable marker (not shown) can be provided on the dilatation catheter and can be set to the distance measured by the calibrater. This indicates the desired catheter insertion distance from the arteriotomy. As soon as the dilatation catheter has been inserted into the desired position, the balloon can be inflated to its maximum size by using the contrast medium to dilate the stenosis to the desired extent. After this has been accomplished, once or twice, the balloon 16 is again deflated and the catheter 11 can be removed and discarded.

In inserting the catheter 11 into the stenosis, the flexible tip 17 which is provided facilitates introduction of the catheter into the stenosis. This is also facilitated by the fact that the distal extremity of the catheter can be rotated to cause rotational movement of the tip 17 by rotating the knob 36.

It is apparent from the foregoing that there has been provided a low-profile steerable intraoperative dilatation catheter which is particularly useful for performing dilations of arteriostenosis which are not amenable to a suitable surgical bypass because of size and location of the lesions. The catheter is constructed in such a manner so that it can be readily utilized by the surgeon during bypass operations. It is of relatively short configuration so that it can be readily manipulated by the physician. Rotation can be readily imparted to the tip by rotation of a knob. Because of the relatively short length of the catheter, there is sufficient torsional rigidity in the core wire so that there is almost a one-to-one correspondence between rotation of the knob and rotation of the tip of the catheter. The catheter is constructed in such a manner so that the tip cannot pop out or be pulled out accidentally.

What is claimed is:

1. In a low-profile steerable intraoperative balloon dilatation catheter, a flexible core wire having proximal and distal extremities, a flexible tubular member extending over the core wire and having proximal and distal extremities with the distal extremity being bonded to the distal extremity of the core wire to form a liquid-tight seal, a balloon carried by the distal extremity of the flexible tubular member, the flexible tubular member providing a lumen extending from the proximal end of the flexible tubular member and extending into the balloon, and an adapter secured to the proximal ends of the core wire and the flexible tubular member, the adapter having at least first and second arms with the core wire extending through the first arm and the lumen being in communication with the second arm, means carried by the first arm and secured to the core wire for permitting rotation of the core wire while limiting movement longitudinally of the axis of the core wire, the catheter having a length so that there is approximately a one-to-one correspondence in rotation of the tip of the core wire with the rotation of the core wire at the proximal extremity.

2. A catheter as in claim 1 wherein said means carried by the first arm and for rotating the core wire includes a knob rotatably mounted upon the arm and wherein said means for limiting movement longitudinally of the axis of the core wire includes a member secured to the knob together with an additional member carried by the first arm and secured to the first arm and being engagable by said member to prevent axial movement of said knob with respect to said first member.

3. A catheter as in claim 1 wherein said catheter has a length of approximately 40 centimeters.

4. A catheter as in claim 1 together with a removable protective sheath disposed over the distal extremity and serving to protect said balloon.

* * * * *